United States Patent [19]
Niki et al.

[11] Patent Number: 4,541,908
[45] Date of Patent: Sep. 17, 1985

[54] HEME PROTEIN IMMOBILIZED ELECTRODE AND ITS USE

[75] Inventors: Katsumi Niki, Yokohama; Hiroo Inokuchi, Okazaki; Tatsuhiko Yagi, Shizuoka; Asao Nakamura, Tokyo, all of Japan

[73] Assignee: Ajinomoto Company Incorporated, Tokyo, Japan

[21] Appl. No.: 646,072

[22] Filed: Aug. 31, 1984

Related U.S. Application Data

[63] Continuation-in-part of Ser. No. 562,030, Dec. 15, 1983, which is a continuation-in-part of Ser. No. 385,315, Jun. 4, 1982, abandoned.

[30] Foreign Application Priority Data

Jun. 12, 1981 [JP] Japan .................................. 56-89615

[51] Int. Cl.³ .......................... C25B 1/02; C25B 11/04
[52] U.S. Cl. .................................... 204/101; 204/129; 204/290 R; 204/291; 204/294; 204/DIG. 4; 427/414; 429/43
[58] Field of Search ................... 204/129, 290 R, 291, 204/101, DIG. 4, 294; 429/43; 427/414

[56] References Cited

U.S. PATENT DOCUMENTS

| | | | |
|---|---|---|---|
| 3,226,262 | 12/1965 | Rohrback et al. | 136/86 |
| 3,403,081 | 9/1968 | Rohrback et al. | 204/1 |
| 4,439,302 | 3/1984 | Wrighton et al. | 204/290 R |

FOREIGN PATENT DOCUMENTS

| | | |
|---|---|---|
| 2049008 | 4/1972 | Fed. Rep. of Germany . |
| 1303200 | 7/1962 | France . |
| 1361241 | 4/1964 | France . |
| 2495843 | 6/1982 | France . |
| WO80/00453 | 3/1980 | PCT Int'l Appl. . |

OTHER PUBLICATIONS

Tarasevich, M. R. and Bogdanovskaya, "The Influence of Hem-Containing Proteins and Their Active Sites on the Electro-Reduction of Molecular $O_2$," Bioelectrochemistry and Bioenergetics 2, 69–78, (1975).

M. R. Tarasevich et al., "Electrocatalysis of Oxygen Reduction on Organic Metallic Complexes," Bioelectrochemistry and Bioenergetics 4, 18–29 (1977).

M. R. Tarasevich et al., "Electrocatalysis of a Cathodic Oxygen Reduction," Bioelectrochemistry and Bioenergetics 6, 393–403 (1979).

James P. Collman et al., "Potent Catalysis of the Electroreduction of Oxygen to Water by Dicobalt Porphyrin Dimers Adsorbed on Graphite Electrodes," J. Electroanal. Chem., 101, 117–122 (1979).

James P. Collman et al., "Electrode Catalysis of the Four-Electron Reduction of Oxygen to Water by Dicobalt Face-to-Face Porphyrins," J. Am. Chem. Soc., 102, 6027–6036 (1980).

Jahnke et al., "Cathodic Reduction of Oxygen on Chelates," Chem. Abstracts 91, (20), p. 520 (1979).

Bogdanovskaya et al., "Electrocatalysis for Organic Complexes. I. Electroreduction of Oxygen in the Presence of Iron-Containing Proteins and Their Active Groups," Chem. Abstracts 84 (2), p. 374, (1976).

Yagi et al., "New Assay Method for Hydrogenase Based on an Enzymic Electrode Reaction. Enzymic Electric Cell Method," Chem. Abstracts 83 (21), p. 204 (1975).

Yagi et al., "Separation of Hydrogenase-Catalyzed Hydrogen-Evolution System from Electron-Donating System by Means of Enzymic Electric Cell Technique," Chem. Abstracts 86 (4), p. 178 (1977).

Primary Examiner—R. L. Andrews
Attorney, Agent, or Firm—Oblon, Fisher, Spivak, McClelland & Maier

[57] ABSTRACT

An electrical conducting solid electrode on the surface of which cytochrome $c_3$ is immobilized in an amount ranging from 20%–100% of the monolayer coverage, said electrode thereby provided with the electrocatalytic capability of the direct four-electron reduction of dioxygen to water, and its uses.

17 Claims, 1 Drawing Figure

HEME PROTEIN IMMOBILIZED ELECTRODE AND ITS USE

This application is a continuation-in-part of application Ser. No. 562,030 filed Dec. 15, 1983, which is a continuation-in-part of application Ser. No. 385,315 filed June 4, 1982, now abandoned.

DETAILED EXPLANATION OF THE INVENTION

The invention relates to an electrical conducting solid electrode on the surface of which cytochrome $c_3$ is immobilized, such an electrode being provided with the electrocatalytic activity of the direct four-electron reduction of dioxygen and enzymatic activities, and its uses.

During the last five years, there has been a great deal of interest in the fabrication of chemically modified electrodes or catalytic electrodes. The fabrication of oxygen electrodes catalzying the electrochemical reduction of dioxygen given by the following two schemes:

| Scheme I: | $O_2 + 2e + 2H^+ \rightarrow H_2O_2$ | (a) |
| --- | --- | --- |
| | $H_2O_2 + 2e + 2H^+ \rightarrow 2H_2O$ | (b) |
| Scheme II: | $O_2 + 4e + 4H^+ \rightarrow 2H_2O$ | | is one of the most important subjects in the development of fuel cell technology.

It has been well known that M. R. Tarasevich used electrodes on which either heme protein or laccase is immobilized to catalyze the electrochemical reduction of dioxygen (Bioelectrochemistry and Bioenergetics, 2, 69–78 (1975) and 6, 393–403 (1979)). However, it is not easy to produce them in a large scale plant, because they are of either animal or plant origin.

It has been also well known that metallo (Fe, Co, Mn)-phthalocyanines and -porphyrins and their derivatives catalyze the electrochemical reduction of dioxygen when they are immobilized on solid electrodes. However, dioxygen is only reduced to hydrogen peroxide by the two-electron reaction with these electrodes in a neutral solution.

With the electrode on which dimeric cobalt-porhydrin is immobilized, dioxygen is reduced directly to water only in a solution of strong acid such as 1 M perchloric or trichloroacetic acid (J. Electroanalyticl Chemistry, 101, 117–122 (1979); J. American Chemical Society, 102, 6027-6–36 (1980)). With the electrode on which either one of metallo (Co, Mn, Fe)-phthalocyanine complexes or Fe-protoporphyrin is immobilized, dioxygen is reduced directly to water only in a strong alkaline solution, e.g., at pH 12 (Bioelectrochemistry and Bioenergetics, 4, 18–29 (1977)). In these electrochemical reactors or cells, dioxygen is reduced directly to water so that the electrolytic solutions are diluted by the produced water.

One of the objects of this invention is to provide electrocatalytic electrodes on the surface of which cytochrome $c_3$ is immobilized with a specified surface coverage, whereby the above-mentioned disadvantages are solved during the reduction of dioxygen.

The invention is hereinafter more fully described and illustrated.

An electrode of this invention comprises an electrical conducting solid electrode material, on which cytochrome $c_3$ is immobilized, with a surface coverage of between 20% and 100% of the monolayer coverage, whereby it is provided with the electrocatalytic activity of the direct four-electron reduction of dioxygen.

The electrodes of this invention show high performance as an oxygen electrode in the direct four-electron reduction of dioxygen. The electrodes also are applicable in the electrolysis of water to oxygen and hydrogen under appropriate conditions.

One of their most important features is to show catalytic activity for the direct four-electron reduction of dioxygen to water in electrolytic solutions having a pH around 7.

Another object of this invention is to provide a method of the direct reduction of dioxygen to water with the use of an electrode of this invention. In greater detail, it is to provide a method of the catalytic four-electron reduction of dioxygen directly to water in an aqueous solution which comprises carrying out said reduction in an aqueous electrolytic solution having a pH of between 4 and 10, with the use of an oxygen electrode comprising a solid electrical conducting material covered with an immobilized cytochrome $c_3$ in an amount ranging from 20% to 100% of the monolayer coverage.

A further object of this invention is to provide a method of electrolysis of water to oxygen and hydrogen with the use of an electrode comprising a solid electrical conducting material covered with an immobilized cytochrome $c_3$ in an amount ranging between 20% and 100% of the monolayer coverage.

Other objects will be apparent from the following disclosure.

Cytochrome $c_3$ employed in this invention is a well-known biological component and may be extracted from, for example, a Desulfovibrio. Six different cytochromes $c_3$ have been isolated and well-characterized in connection with their chemical structure. The three-dimensional structure of two out of the six cytochromes $c_3$ have further been characterized by X-ray diffraction (J. Biochemistry, 87, 1747–1756 (1980) and 89, 1659-1662 (1981); and Nature 282, 806–810 (1979)). It is shown in the literature that the four iron-porphyrins are exposed on the surface of the molecule. It is considered that the heme proteins with this type of structure show a good electrocatalytic activity for the reduction of dioxygen when they are immobilized on solid electrodes. On the other hand, the molecule containing iron porphyrin surrounded by a peptide chain such as cytochrome c shows no or a weak catalytic activity for the reduction of dioxygen.

Examples of Desulfovibrio from which cytochrome $c_3$ is obtained include *Desulfovibrio vulgaris* Miyazaki, *Desulfovibrio vulgaris* Hildenborough, *Desulfovibrio gigas, Desulfovibrio desulfuricans* Norway, *Desulfovibrio desulfuricans* and *Desulfovibrio salexigens*.

The electrical conducting solid electrodes employed in this invention are, for example, metal electrodes such as gold, platinum, nickel, etc, and carbonaceous electrodes such as amorphous carbon, graphite, etc.

The immobilization of cytochrome $c_3$ onto the surface of a solid electrode can be made, e.g., simply by soaking the electrode, the surface of which has been activated for a certain period of time in a phosphate buffer solution of cytochrome $c_3$ at pH 7.0.

The method of activation of the electrode surface is not critical. Metal electrodes are activated, e.g., by treating in a dilute nitric acid. Carbonaceous electrodes can be activated, e.g., by the plasma etching method under an atmosphere of argon, carbon dioxide or oxygen, or under vacuum. The above pretreatments to activate the surface of solid electrodes are a preferable treatment, but are not always imperative.

According to this invention, electrodes have to be covered with cytrochrome $c_3$ in a range from 20% to 100% of the monolayer coverage, preferably in a range from 20% to 80%, to give a good catalytic activity. The best catalytic activity is attained when the surface of the electrodes is covered in a range from 40% to 70% of the monolayer coverage.

The degree of the surface coverage of solid electrodes by cytochrome $c_3$ is one of the most important points to attain a good electrocatalytic activity in the direct four-electron reduction of dioxygen to water. When the electrode surface is covered with cytochrome $c_3$ in the above-mentioned range, the efficiency of the direct four-electron reduction of dioxygen or the oxidation of water is very high.

The degree of the surface coverage of electrodes varies with the effective surface area of the electrodes, the concentration of cytochrome $c_3$ in the buffer solution, and the duration of soaking of the electrodes in the cytochrome $c_3$ solution.

As will be seen from EXAMPLE 1, the surface coverage of a graphite electrode, which had been plasma etched under vacuum, by cytochrome $c_3$, was about 50% of the monolayer coverage when the elctrode was soaked in a $1 \times 10^{-7}$ M cytochrome $c_3$ solution for half an hour.

As will be seen from EXAMPLE 2, 100% of the monolayer coverage was attained when the electrode was soaked in a $1 \times 10^{-4}$ M cytochrome $c_3$ solution for an hour.

In this connection, the amount of the immobilized cytochrome $c_3$ on an electrode surface is evaluated easily, e.g., by measuring the amount of electricity to reduce the ferri-form cytochrome $c_3$ to the ferro-form.

Both gold and platinum were found to be appropriate substrates as the electrode material.

As is evident from the examples, dioxygen may be reduced directly to water on the electrodes, which have been prepared by the procedure given in the foregoing, without the formation of hydrogen peroxide as an intermediate product in a buffer solution with pH between 7 and 10, preferably in nearly neutral solutions.

The present findings are not predictable from the technologies concerned and experimental results which have been publicized. According to the prior art, dioxygen is reduced to either hydrogen peroxide in neutral solutions or water directly only in strong acid or strong alkaline solutions. Further, it is to be noted that the fraction of the direct four-electron reduction of dioxygen becomes smaller with electrodes covered by multilayers of cytochrome $c_3$, compared with the monolayer coverage or less. Indeed, it has been reported that dioxygen is reduced directly to water on a dropping mercury electrode with the cytochrome $c_3$ absorbed layer. However, mercury is not practical as an electrode material because it is liquid and also it is poisonous.

Known catalysts such as heme proteins and laccase are not practical catalysts because a large scale production of these catalysts is impractical. On the other hand, a Desulfovibrio can be easily found anywhere naturally and isolated and large scale production of a Desulfovibrio is very easy (Kagaku, 51, [6] 369–376 (1981)). Also, cytochrome $c_3$ is advantageous as a practical catalyst for the direct four-electron reduction of dioxygen. The absorbed layer of cytochrome $c_3$ onto the surface of a solid electrode is stable and cytochrome $c_3$ is not poisonous.

Carbonaceous electrodes as a substrate are inexpensive and are easy to fabricate. At the present time, the evolution of hydrogen or the dissociation reaction of hydrogen is usually carried out with the use of a catalyst such as iron, carbon or a noble metal such as silver or platinum. However, the use of noble metals is limited by their scarcity and expense.

Cytochrome $c_3$ and hydrogenase as employed in accordance with this invention are more advantageous from the point of view of both their resources and functions. Additionally, as is evident from EXAMPLE 8 and EXAMPLE 10, their activity is more than 30 times that of a commonly used carbon electrode.

DESCRIPTION OF THE DRAWINGS

FIG. 1 (right side) depicts a typical arrangement of the electrode, the electrolyte, the counter electrode, the salt bridge, a reference electrode, and a gas trap for collecting the gas which is evolved during operation of the cell. Also indicated in the drawing is the possibility that the cell may be connected to a potentiogalvanostat.

Figure 1:
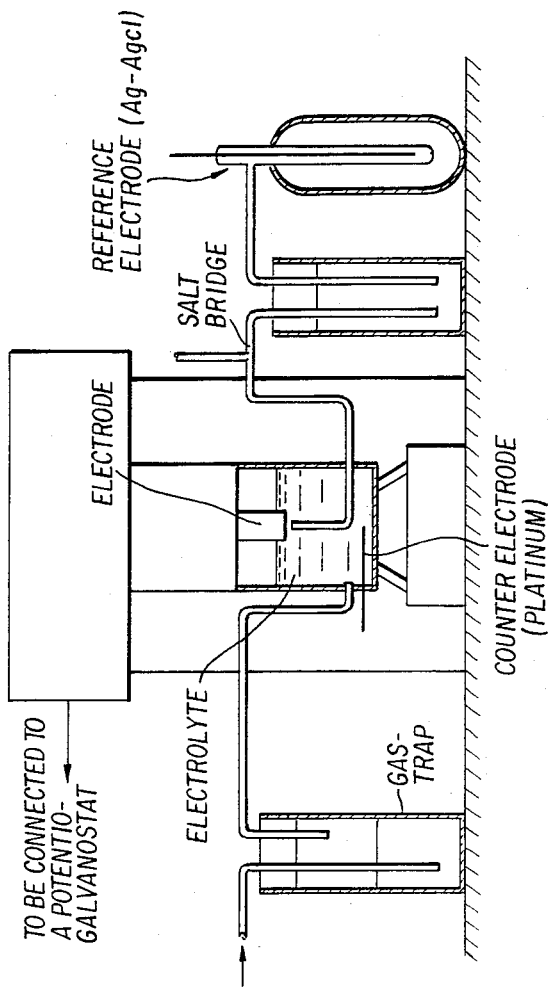
FIG. 1 (left side) shows the arrangement of a ring electrode and a disk electrode of the present invention. The top arrow indicates the direction of rotation of the electrode.
Figure 1:
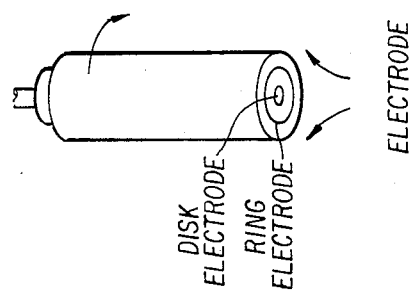

The invention is further illustrated with reference to the following examples and comparative experiments, but not intended to be restricted by them.

EXAMPLE 1

A graphite electrode was pretreated by radio frequency plasma under vacuum so that a more than 100-fold surface area was generated.

The pretreated graphite electrode (surface area $2 \times 2$ cm$^2$) was soaked in a $1 \times 10^{-7}$ M cytochrome $c_3$ buffer solution having a pH of 7 (phosphate buffer) for half an hour and about 50% of the surface was covered with cytochrome $c_3$. The cytochrome $c_3$ had been extracted from a *D. vulgaris* Miyazaki strain.

Dioxygen in a phosphate buffer solution (pH 7.0) saturated with air was reduced by using a graphite electrode as the oxygen electrode.

Only water was the reduction product, and no hydrogen peroxide was detectable.

EXAMPLE 2

Cytochrome $c_3$ was immobilized on a graphite electrode described in EXAMPLE 1 by soaking it in a $1 \times 10^{-4}$ M cytochrome $c_3$ solution (pH 7.0) for an hour and a monolayer was formed on the surface of the electrode.

The electrochemical reduction of dioxygen was carried out in the same way as given in EXAMPLE 1. The fraction of the four-electron reduction of dioxygen was 80%.

EXAMPLE 3

A similar catalytic activity to that of the Miyazaki strain for the reduction of dioxygen was shown when EXAMPLE 1 was repeated using cytoochrome $c_3$ extracted from a *Desulfovibrio vulgaris* Hildenborough strain instead of that extracted form the former strain.

EXAMPLE 4

Monolayer coverage was attained when a gold electrode (surface area $1 \times 2$ cm$^2$) was soaked in a $1 \times 10^{-4}$ M cytochrome c$_3$ solution for 10 minutes. The cytochrome c$_3$ layer was stable and could be removed only when the electrode was cycled between the hydrogen evolution and oxygen evolution potentials.

EXAMPLE 5

The oxidation of water on a gold electrode corresponds to the formation of gold oxide on the electrode. On the other hand, with a gold electrode covered by cytochrome c$_3$ the oxidation potential of gold shifted more positive. But, the amount of electricity for the oxidation of water was about 20% more than the amount for the reduction of gold oxide. That difference between the amounts of electricity corresponds to the evolution of oxygen.

COMPARATIVE EXPERIMENT 1

The same pretreated graphite electrode as illustrated in EXAMPLE 1 but covered by multilayers of cytochrome c$_3$ was prepared by soaking the carbon substrate in a $1 \times 10^{-4}$ M cytochrome c$_3$ solution for more than 48 hours.

The fraction of the four-electron reduction of dioxygen was 30%.

COMPARATIVE EXPERIMENT 2

The fraction of the four-electron reduction of dioxygen was less than 20% with the same pretreated graphite electrode as illustrated in EXAMPLE 1 but covered by the monolayer consisting of 50% cytochrome c$_3$ and 50% cytochrome c.

EXAMPLE 6

Cytochrome c$_3$ extracted from *D. vulgaris*, Miyazaki F, was dissolved in a phosphate buffer solution (pH=7.0) to prepare a $1 \times 10^{-7}$ M cytochrome c$_3$ buffer solution. The prepared solution was put dropwise onto the gold disk electrode of a rotating ring disk electrode and the cytochrome c$_3$ was adsorbed for 30 minutes, whereby about 50% of the surface of the electrode was covered with cytochrome c$_3$.

Oxygen reduction was measured with the use of the rotating ring disk electrode apparatus as shown in FIG. 1, wherein a phosphate buffer solution (pH=7.0) saturated with oxygen gas was used and the above-mentioned electrode was used as the oxygen electrode.

The oxygen was quantitatively reduced directly to water, and no hydrogen peroxide was detectable, as shown in Table 1.

On the other hand, if a gold electrode not covered with cytochrome c$_3$ was used, some ring current was observed, and the oxygen was reduced only to hydrogen peroxide, as shown in Table 2.

TABLE 1

| | Electrode with Cytochrome C$_3$ | |
|---|---|---|
| Voltage (V) | Disk Current (mA/cm$^2$) | Ring Current (mA/cm$^2$) |
| +0.2 | 0 | 0 |
| 0 | 2.8 | 0 |
| −0.2 | 4.5 | 0 |
| −0.4 | 4.6 | 0 |
| −0.6 | 5.0 | 0 |
| −0.8 | 5.8 | 0 |
| −1.0 | 7.0 | 0 |

TABLE 2

| | Electrode without Cytochrome C$_3$ | |
|---|---|---|
| Voltage (V) | Disk Current (mA/cm$^2$) | Ring Current (mA/cm$^2$) |
| +0.2 | 0 | 0 |
| 0 | 1.4 | 0.4 |
| −0.2 | 2.3 | 0.6 |
| −0.4 | 2.6 | 0.6 |
| −0.6 | 3.2 | 0.3 |
| −0.8 | 4.1 | 0.1 |
| −1.0 | 6.3 | 0 |

EXAMPLE 7

Cytochrome c$_3$ extracted from *D. vulgaris*, Miyazaki F, was dissolved in a phosphate buffer solution (pH=7) to prepare a $1 \times 10^{-4}$ M cytochrome c$_3$ buffer solution. An SAPG (stress-annealed pyrolytic graphite) electrode was soaked in the prepared solution for about an hour, whereby the electrode was covered with a monolayer of cytochrome c$_3$.

Oxygen reduction was measured by cyclic voltammetry, wherein a phosphate buffer solution (pH=7) saturated with oxygen gas and the above-mentioned electrode was used as the oxygen electrode.

When the elctrode covered with cytochrome c$_3$ was used, about 50% of the oxygen was reduced directly to water and the remaining oxygen was reduced to hydrogen peroxide.

On the other hand, when a graphite electrode not covered with cytochrome c$_3$ was used, the oxygen was reduced only to hydrogen peroxide.

The results are listed in Table 3.

TABLE 3

| Voltage (V) | Current ($\mu$A/cm$^2$) A* | B** |
|---|---|---|
| +0.2 | 0 | 0 |
| 0 | 0 | 0 |
| −0.2 | 229 | 180 |
| −0.4 | 560 | 430 |
| −0.6 | 580 | 450 |
| −0.8 | 700 | 720 |
| −1.0 | 850 | 860 |

*Covered with cytochrome c$_3$
**Not covered with cytochrome c$_3$

EXAMPLE 8

As in EXAMPLE 7, an electrode covered with a monolayer of cytochrome c$_3$ was made.

First, the gold electrode was soaked in a 0.03 M phosphate buffer solution (pH=7) well deaerated with argon gas, and the cyclic voltammogram was measured at a sweep rate of 2 mv/second. The results are shown in Table 4, Column A.

On the other hand, the electrode was soaked in a mixed solution of 100 $\mu$l cytochrome c$_3$ solution ($3.4 \times 10^{-5}$ M), 500 $\mu$l hydrogenase solution ($2.5 \times 10^{-5}$ M) and 2 ml 0.03 M phosphate buffer solution (pH=7.0), and the dissociation of hydrogen was measured by voltammetry under the conditions of bubbling hydrogen gas at a rate of 2.5 ml/minute. The results are shown in Table 4, Column B.

It can be understood from the Table that remarkably much more current can be obtained with a cytochrome $c_3$-covered electrode than with a non-cytochrome $c_3$-covered electrode.

TABLE 4

| Voltage (V) | Current ($\mu A/cm^2$) | |
|---|---|---|
| | A | B |
| 0 | 0 | 0 |
| 0.2 | 2.8 | 3.6 |
| 0.4 | 3.5 | 14.3 |
| 0.6 | 4.3 | 28.6 |
| 0.8 | 4.8 | 57.2 |
| 0.9 | 5.7 | 107.1 |
| 0.95 | 7.1 | 197.1 |

EXAMPLE 9

Under the same conditions as in EXAMPLE 8, a gold electrode covered with a monolayer of cytochrome $c_3$ was made.

First, the gold electrode was soaked in a phosphate buffer solution well deaerated with argon gas, and the cyclic voltammogram was measured. The results are shown in Table 5, Column A.

On the other hand, the electrode was soaked in a mixed solution of 100 $\mu l$ cytochrome $c_3$ solution ($3.4 \times 10^{-3}$ M), 500 $\mu l$ hydrogenase solution ($2.5 \times 10^{-5}$ M) and 0.03 M phosphate buffer solution (pH=7), and then well deaerated with argon gas. The evolution of hydrogen was measured by cyclic voltammetry at a sweep rate of 2 mv/second. The results are shown in Table 5, Column B.

TABLE 5

| Voltage (V) | Current ($\mu A/cm^2$) | |
|---|---|---|
| | A | B |
| 0 | 0 | 0 |
| −0.2 | 5.3 | 10.6 |
| −0.4 | 10.6 | 28.3 |
| −0.6 | 14.2 | 42.4 |
| −0.8 | 21.2 | 77.8 |
| −0.9 | 35.4 | 143 |
| −0.95 | 60.1 | 376 |

EXAMPLE 10

As in EXAMPLE 7 an electrode covered with a monolayer of cytochrome $c_3$ was made.

First, the gold electrode was soaked in a 0.03 M phosphate buffer solution (pH=7.0) well deaerated with argon gas, and the cyclic voltammogram was measured at a sweep rate of 2 mv/s.

The results are shown in Table 6, Column A.

On the other hand, the electrode was soaked in a mixed solution of 100 $\mu l$ cytochrome $c_3$ solution ($3.4 \times 10^{-3}$ M), 500 $\mu l$ hydrogenase solution ($2.5 \times 10^{-5}$ M) and hydrogenase was well activated by means of bubbling hydrogen gas and a flowing amount of coulombs which were sufficient to reduce hydrogenase, and then the dissociation of hydrogen gas was measured by cyclic voltammogram under the condition of bubbling hydrogen gas at a rate of 2.5 ml/m.

The results are shown in Table 6, Column B.

TABLE 6

| Voltage (V) | Current ($\mu A/cm^2$) | |
|---|---|---|
| | A | B |
| −0.6 | 0 | 0 |
| −0.5 | 0 | 2 |
| −0.4 | 0 | 6 |
| −0.3 | 0 | 25 |
| −0.2 | 1.2 | 60 |

Almost the same results are obtained in the hydrogenase solution, using the electrode on the surface of which cytochrome $c_3$ is immobilized by an appropriate method. For example, cytochrome $c_3$ is immobilized by an irreversible adsorption onto the surface of various solid electrodes such as carbon, gold, etc., or immobilized by covalent bonding, for instance, using polyvinylpyridine, etc. (J. Am. Chem. Soc, 102, 2452 (1980))

It is obvious from the foregoing examples and comparative experiments that the role of cytochrome $c_3$ is remarkable as a catalyst for the four-electron reduction of dioxygen when cytochrome $c_3$ is immobilized on the surface of various electrical conduction solid materials. It is also obvious that a cytochrome $c_3$-immobilized electrode when used together with enzyme such as hydrogenase is remarkably useful for the evolution or dissociation of hydrogen.

What is claimed is:

1. An electrode comprising a solid electrical conducting material on the surface of which cytochrome $c_3$ is immobilized in an amount ranging between 20% and 100% of monolayer coverage.

2. A method of catalytic four-electron reduction of dioxygen directly to water in an aqueous solution which comprises placing an oxygen electrode comprising a solid electrical conducting material on the surface of which cytochrome $c_3$ is immobilized in an amount ranging between 20% and 100% of monolayer coverage into a first aqueous electrolyte solution at a pH of from about 4 to 10, placing a second electrode into a second aqueous electrolyte solution, said second electrolyte solution and second electrode being in communication with said first electrolyte solution and said first electrode in a manner to complete an electrical circuit, and applying an electrical current to said circuit sufficient to cause reduction of oxygen to water at the first electrode.

3. The method as claimed in claim 2 in which said oxygen electrode is a carbon electrode on the surface of which cytochrome $c_3$ is immobilized in an amount ranging from 40% to 70% of monolayer coverage, said cytochrome $c_3$ being isolated from a microorganism of the genus Desulfovibrio which is capable of producing cytochrome $c_3$.

4. A method of electrolysis of water to oxygen and hydrogen with the use of the electrode as claimed in claim 1 which comprises
   placing said electrode into a first aqueous electrolyte solution,
   placing a second electrode into a second aqueous electrolyte solution, said second electrolyte solution and said electrode being in communication with said first electrolyte solution and said first electrode in a manner to complete an electrical circuit, and
   applying an electrical current to said circuit sufficient to cause electrolysis of water to oxygen and hydrogen.

5. A method of producing hydrogen which comprises placing an electrode as set forth in claim 1 in a mixed solution comprising (1) a buffer solution and (2) an electrolyte solution containing a redox compound which couples with cytochrome $c_3$ in a hydrogen evolution reaction, and placing a second electrode into a second aqueous electrolyte solution, said second electrolyte solution and said second electrode being in communication with said first electrolyte solution and said mixed solution in a manner to complete an electrical circuit, and applying an electrical current to said circuit sufficient to cause hydrogen evolution at the first electrode.

6. The method of claim 5, wherein said redox compound which couples with cytochrome $c_3$ is hydrogenase, nitrogenase or a ferredoxin.

7. A method of dissociating hydrogen which comprises placing an electrode as set forth in claim 1 as a hydrogen electrode in a mixed solution comprising (1) a buffer solution and (2) an electrolyte solution containing a redox compound which couples with cytochrome $c_3$ in a hydrogen dissociation reaction and placing a second electrode into a second aqueous electrolyte solution, said second electrolyte solution and said second electrode being in communication with said first electrolyte solution and said first electrode in a manner to complete an electrical circuit, and applying an electrical current to said circuit sufficient to cause dissociation of hydrogen at the first electrode.

8. The method of claim 7, wherein said redox compound which couples with cytochrome $c_3$ is hydrogenase, nitrogenase or a ferredoxin.

9. The method of claim 7, wherein said hydrogen electrode is an anode of a fuel cell.

10. An electrode comprising a solid electrical conducting material on the surface of which cytochrome $C_3$ is immobilized in an amount ranging from about 20%–100% of monolayer coverage which is prepared by soaking said electrode in a solution comprising cytochrome $C_3$ in a concentration of from about $10^{-5}$ M to $10^{-3}$ M.

11. An electrode comprising a solid electrical conducting material on the surface of which cytochrome $C_3$ is immobilized in an amount ranging from about 20%–100% of monolayer coverage which is further treated by:

(a) soaking the electrode in a solution comprising hydrogenase, and (b) activating the hydrogenase.

12. The electrode of claim 11 wherein the cytochrome $C_3$ is immobilized by irreversible adsorption onto the electrode.

13. The electrode of claim 11 wherein the cytochrome $C_3$ is immobilized by covalent bonding.

14. The electrode of claim 13 wherein the covalent bonding is effected with polyvinylpyridine.

15. An electrode comprising a solid electrical conducting material on the surface of which cytochrome $C_3$ is immobilized in an amount ranging from about 20-100 percent of monolayer coverage which is prepared by:

(a) soaking the electrode in a mixed solution containing cytochrome $C_3$ and hydrogenase, and (b) activating the hydrogenase.

16. The electrode of claim 15 wherein the hydrogenase is activated by means of bubbling hydrogen gas.

17. The electrode of claim 15 wherein the concentration of cytochrome $C_3$ in the mixed solution is approximately $10^{-5}$ M.

* * * * *